ROSE PLANT SEEDLING 69-23R
Filed March 21, 1975
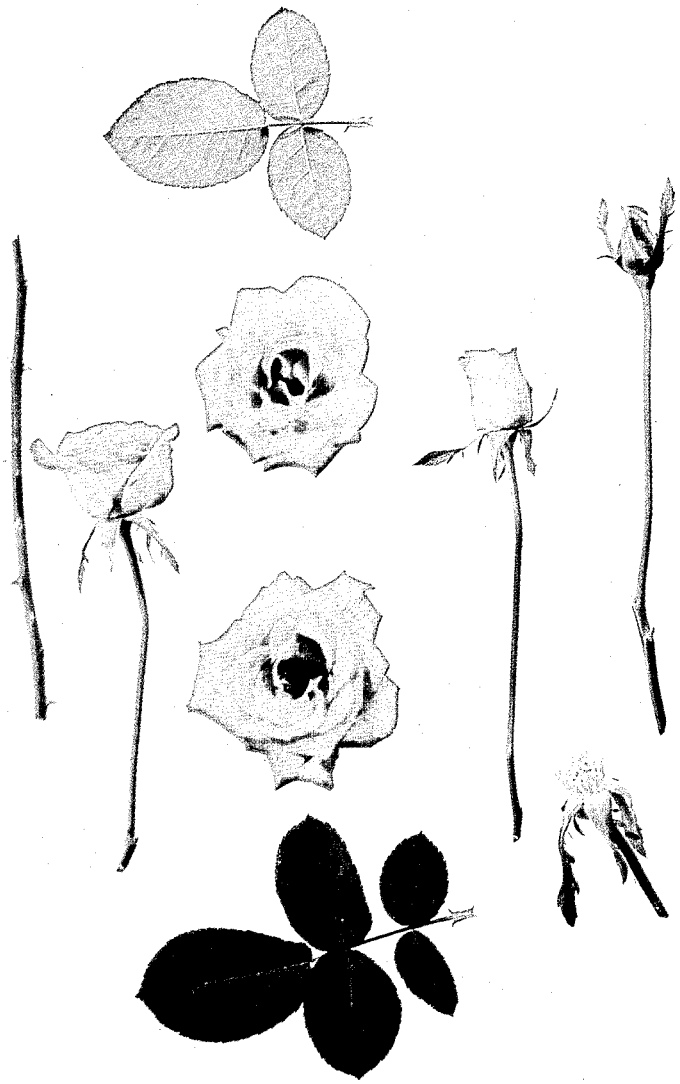

United States Patent

Plant Pat. 3,902

Patented June 8, 1976

3,902

ROSE PLANT SEEDLING 69—23R

Roy L. Byrum, Richmond, Ind., assignor to Joseph H. Hill Company, Richmond, Ind.

Filed Mar. 21, 1975, Ser. No. 560,693

Int. Cl. A01h *5/00*

U.S. Cl. Plt.—28 1 Claim

ABSTRACT OF THE DISCLOSURE

A new variety of hybrid rose for greenhouse production of cut flowers for the commercial market, distinguished by its vigorous upright growth and its abundant and continuous production of solid red flowers which are borne on strong, straight stems of good commercial length and which have excellent keeping qualities at living room temperature.

BACKGROUND OF THE NEW PLANT

My new variety of rose plant was produced by my crossing of "Cotillion" (P.P. 2,978), as seed parent, with "Suspense" (P.P. 1,944) in 1968 with the object of developing a free-blooming variety of the floribunda type having less of the novelty characteristics of its parents, particularly its seed parent "Cotillion," and a more uniform, solid red color of a kind to find strong demand in the commercial market. This plant originated as a seedling resulting from the said crossing and was selected because of its strong growth habit, the excellent color of its well-formed flowers, and its abundant flower production and asexual propagation of this plant by budding, under my direction at Richmond, Ind., and at Hamilton City, Calif., has demonstrated that its novel characteristics are firmly fixed and hold true from generation to generation.

DESCRIPTION OF THE DRAWING

My new variety of rose plant is illustrated by the accompanying photographic drawing made from specimens taken from a plant in full bloom in January 1975 and which shows, in full color, the form of the opened flower and several stages of the bud, top and underside view of typical leaves, and a specimen of the wood, the colors shown being as nearly true as reasonably possible to obtain by conventional photographic procedures.

DESCRIPTION OF THE NEW PLANT

The following is a detailed description of my new variety of rose plant with color designations according to Robert F. Wilson's Horticultural Colour Chart (W), published by the Royal Horticultural Society at London, England, and in some instances by Koster's Color Guide (K), all observations having been made from plants and flowers grown in greenhouse at Richmond, Ind.

THE PLANT

Origin: Seedling.

Parentage:

*Seed parent.*—Cotillion (Plant Pat. 2,978).

*Pollen parent.*—Suspense (Plant Pat. 1,944).

Classification:

*Botanical.*—Rosa hybrid.

*Commercial.*—Floribunda.

Form: Bush.

Habit: Upright and much branched.

Growth: Free and vigorous.

Main stems: Color—Olive Green, (K) Plate 84, with streaks of Dark Violet, (K) Plate 58.

*Thorns.*—Several, short and downwardly hooked and with a short, narrow base. Color: Dark Violet, (K) Plate 58.

*Prickles and hairs.*—None.

Branches: Color—Spinach Green, (W) 0960.

*Thorns.*—Several, short and downwardly hooked with a short, narrow base. Color: Amaranth Red, (K) Plate 43.

*Prickles.*—Few. Color: Amaranth Red, (K) Plate 43.

*Hairs.*—None.

New shoots: Color—Lettuce Green, (W) 861/2.

*Thorns.*—Several, short and hooked downwardly and with a short, narrow base. Color: Carmine Rose, (W) 621/2.

*Prickles and hairs.*—None.

Foliage: Quantity—abundant.

*Leaves.*—Size—Medium and heavy. Shape—Odd pinnate.

*Leaflets.*—3 or 5 in number. Shape: Ovoid, with acute apex, round base and simply serrate margins. Texture: Leathery. Color: Mature, upper surface—Spinach Green, (W) 0960 (nearest color). Mature, under surface—Apple Green, (K) Plate 77 (nearest color). Young, upper surface—Scheeles Green, (W) 860/1, with leaf margins bordered with Oxblood Red, (W) 00823/3 (nearest colors). Young, under surface—Scheeles Green, (W) 860/3 (nearest color).

Rachis: Medium heavy, grooved upper side and moderately prickly under side.

Stipules: Short and narrow with very short points which are turning out at an angle of more than 45°.

THE BUD

Before calyx breaks:

*Size.*—Medium small.

*Form.*—Short pointed, with a conspicuous neck and with foliaceous appendages on the surface of the bud which extend beyond the bud tip a distance equal to ¼ or more of the bud length.

*Color calyx.*—Scheeles Green, (W) 860/2.

As calyx breaks:

*Color of bud.*—Ruby Red, (W) 827.

As first petals open:

*Size.*—Medium small.

*Form.*—Short pointed.

*Color of petal.*—Outside—Cardinal Red, (W) 822/2, overlaid with shades of Chrysanthemum Crimson, (W) 824/2. Inside—Cardinal Red, (W) 822/2, overlaid with a dark velvety sheen of Chrysanthemum Crimson, (W) 824.

Bud opening: Bud opens up well in greenhouse.

Sepals: Permanent, of medium length, spear-shaped and curving backward and downward as bud opens up.

*Color.*—Inside—Scheeles Green, (W) 860/1, overlaid with white fuzz. Outside—Scheeles Green, (W) 860/1.

Peduncle: Strong, erect, of medium diameter and length.

*Bark.*—Smooth. Color: Scheeles Green, (W) 860.

*Thorns.*—None.

*Prickles and hairs.*—None.

THE FLOWER

Blooming habit: Free, abundantly and continuous.

Size: Medium. 2 to 3 inches in diameter when fully opened.

Borne: Usually singly, but often two or three blooms on a strong stem of medium length which is disbudded to one for commercial purposes.

Shape: High centered at first with petals tightly rolled outward; becoming open with petals loosely rolled outward at maturity.

Petalage: Double, with 25 to 30 petals regularly arranged.

*Shape.*—Outside and intermediate petals.—Ovate with retuse apex. Inside petals—Ovate, most with retuse apex, some with 1 or 2 notches.

*Aspect.*—Inside—Velvety; Outside—Satiny.

*Texture.*—Moderately thick.

Color:

A. The following are observations of a flower newly opened in November 1974.

*Outside petals.*—Outer surface—Rose Bengal, (W) 25/1, with very light veins of Rose Bengal (W) 25/2, and base of Mimosa Yellow, (W) 602/2. Inside surface—Rose Red, (W) 724, (nearest color), with a light velvety sheen. Base is Mimosa Yellow, (W) 602/2.

*Intermediate petals.*—Outer surface—Rose Bengal, (W) 25. Base of Mimosa Yellow, (W) 602/2. Inside surface — Rose Red, (W) 724 (nearest color), with base of Mimosa Yellow, (W) 602/1.

*Inner petals.*—Outer and inner surfaces—Rose Bengal, (W) 25. Some petals have a white streak through the center of the outer surface. Petal base is Mimosa Yellow, (W) 602/1.

B. The following are observations of a flower opened three days in November 1974.

*Outside petals.*—Outer surface—Rose Bengal, (W) 25/1, with veins of Rose Bengal, (W) 25/3. Base color is Barium Yellow, (W) 503/2. Inside surface—Rose Red, (W) 724/2 (nearest color), overlaid with shade of Rose Red, (W) 724, and a slight velvety sheen. Base is Barium Yellow, (W) 503/2.

*Intermediate petals.*—Outer surface—Rose Madder, (W) 23/1, with very light veins of Rose Madder, (W) 23/2, and Barium Yellow, (W) 503/2, at base. Inside surface—Rose Madder, (W) 23, with very light veins of Rose Madder, (W) 23/2, and with base of Barium Yellow, (W) 503/2.

*Inner petals.*—Outer surface — Rose Madder, (W) 23/1, with very light veins of Rose Madder, (W) 23/2, and base of Barium Yellow, (W) 503/2. Inside surface—Rose Madder, (W) 23, with very light veins of Rose Madder, (W) 23/2, and base of Barium Yellow, (W) 503/2.

General color effect of open bloom:

*Newly opened flower.*—Tyrian Rose, (W) 24.

*Three days open flower.*—Tyrian Rose, (W) 24/1.

Persistence: Petals hang on.

Fragrance: Moderately tea.

Lasting quality: 4 to 6 days at living room temperature in November.

REPRODUCTIVE ORGANS

Stamens: Many in number, regularly arranged about the pistils.

*Filaments.*—Medium length, most having anthers. Color: Egyptian Buff, (W) 407.

*Anthers.*—Medium in size, all open at once. Color: Egyptian Buff, (W) 407/2.

*Pollen.*—Abundant. Color: Chrome Yellow, (W) 605/3.

Pistils: Many in number.

*Styles.*—Short, bunched, moderately thin and of uneven length. Color: Most are Vermillion, (W) 18/2. Some, on outside, are Amber Yellow, (W) 505.

*Stigma.*—Color: Pure White, (K) Plate #1.

This new variety of rose plant is considered to be an improvement over its seed parent, Cotillion (Plant Pat. 2,978), because of the solid red color of its opened flowers, the somewhat larger size of its bud and open flowers, its stronger stems and large foliage. The new plant differs from its pollen parent, Suspense (Plant Pat. 1,944), by its solid coloring, it smaller flowers and the fact that it is a commercial forcing plant of the floribunda type.

The new plant is a strong, vigorous and upright growing plant with an abundance of dark green foliage throughout the entire plant body. It has a good-to-above average cut flower production with a minimal amount of blind canes, especially in the dark winter months. The flowers are borne on straight, sturdy stems of commercial cut flower lengths which are disbudded to carry a single bloom and their keeping qualities as cut flowers are excellent.

I claim:

1. A new and distinct variety of rose plant substantially as herein shown and described, characterized by its vigorous, upright growing habit, its abundant continuous production of solid colored flowers borne on straight, sturdy stems, and by the minimal amount of blind canes.

No references cited.

ROBERT E. BAGWILL, Examiner